(12) United States Patent
Mahoney, III et al.

(10) Patent No.: US 8,006,918 B2
(45) Date of Patent: Aug. 30, 2011

(54) ALTERNATING CURRENT POWERED DELIVERY SYSTEM

(75) Inventors: William Paul Mahoney, III, Liberty Township, OH (US); Fernando Ray Tollens, Cincinnati, OH (US)

(73) Assignee: The Proctor & Gamble Company, Cincinnati, OH (US)

(*) Notice: Subject to any disclaimer, the term of this patent is extended or adjusted under 35 U.S.C. 154(b) by 103 days.

(21) Appl. No.: 12/245,270

(22) Filed: Oct. 3, 2008

(65) Prior Publication Data
US 2010/0084488 A1   Apr. 8, 2010

(51) Int. Cl.
*B05B 1/08* (2006.01)
(52) U.S. Cl. ............... 239/102.2; 239/102.1; 310/317; 310/318; 331/114; 331/116 R
(58) Field of Classification Search ........... 239/4, 102.1, 239/102.2; 310/311, 317, 318; 331/114, 331/116 R, 146
See application file for complete search history.

(56) References Cited

U.S. PATENT DOCUMENTS

| | | | |
|---|---|---|---|
| 4,264,837 A * | 4/1981 | Gaboriaud | 331/116 R |
| 4,336,509 A | 6/1982 | Bernitz | |
| 4,512,933 A | 4/1985 | Harden | |
| 4,532,582 A | 7/1985 | Freeny | |
| 4,901,034 A * | 2/1990 | Frank-Peter | 239/102.2 |
| 4,929,899 A | 5/1990 | Weixelman et al. | |
| 5,283,728 A | 2/1994 | Hobart | |
| 5,518,179 A | 5/1996 | Humberstone et al. | |
| 6,239,668 B1 | 5/2001 | Menna et al. | |
| 6,506,299 B1 | 1/2003 | Pandolfo | |
| 6,629,646 B1 | 10/2003 | Ivri | |
| 6,697,266 B2 | 2/2004 | Poon et al. | |
| 2002/0129813 A1 | 9/2002 | Litherland et al. | |
| 2007/0279952 A1 | 12/2007 | Lanni | |

FOREIGN PATENT DOCUMENTS

| | | |
|---|---|---|
| EP | 0615470 B1 | 12/1995 |
| JP | 22084663 A2 | 3/2002 |
| WO | WO/03/038918 A2 | 5/2003 |
| WO | WO 2008/114044 A1 | 9/2008 |

OTHER PUBLICATIONS

PCT International Search Report, 4 Pages, Mailed Jan. 22, 2010.

* cited by examiner

*Primary Examiner* — Steven J Ganey
(74) *Attorney, Agent, or Firm* — Larry L. Huston; Leonard W. Lewis; Steven W. Miller

(57) ABSTRACT

An air treatment device having a piezoelectric actuator powered by a transformer. The transformer has dual inputs comprising oppositely wound coils and input power signals 180 degrees out of phase. This arrangement provides a stronger drive signal to the actuator.

5 Claims, 2 Drawing Sheets

ALTERNATING CURRENT POWERED DELIVERY SYSTEM

FIELD OF THE INVENTION

The present invention relates to a delivery system for generating liquid active materials, and more particularly to a delivery system having an AC power supply.

BACKGROUND OF THE INVENTION

Electromechanical transducer delivery systems, such as air treatment devices, are well known in the art. These devices deliver liquid active materials, such as perfumes, air fresheners, insecticides and other volatile materials, to the atmosphere Such devices may generate liquid droplets using electromechanical actuation. One method for such distribution is to atomize a liquid by a delivery system comprising a perforate structure. The perforate structure is vibrated, or otherwise excited, by an electromechanical transducer, often in a bending mode. Liquid is supplied to the vibrating perforate structure and sprayed therefrom in droplets upon vibration/excitation of the perforate structure. Such attempts in the art are illustrated by U.S. Pat. Nos. 3,543,122; 3,615,041; 4,479,609; 4,533,082; 4,790,479; 5,518,179; 5,297,734; 6,341,732; 6,378,780; 6,386,462 and WO 02/068,128.

These devices may be powered by line voltage or by a battery. Battery power provides the convenience of portability and placement away from a wall outlet without the need for an extension cord. However, battery powered devices have the drawback of limited power being available to drive the transducer and limited battery life. Thus, a need exists for an improved delivery system and an associated method for generating droplets of liquid active materials.

SUMMARY OF THE INVENTION

The invention comprises an air treatment device having a piezoelectric actuator powered by a transformer. The transformer has dual inputs comprising oppositely wound coils and signals 180 degrees out of phase. This arrangement provides a stronger drive signal to the actuator.

DETAILED DESCRIPTION OF THE INVENTION

Figure 1:
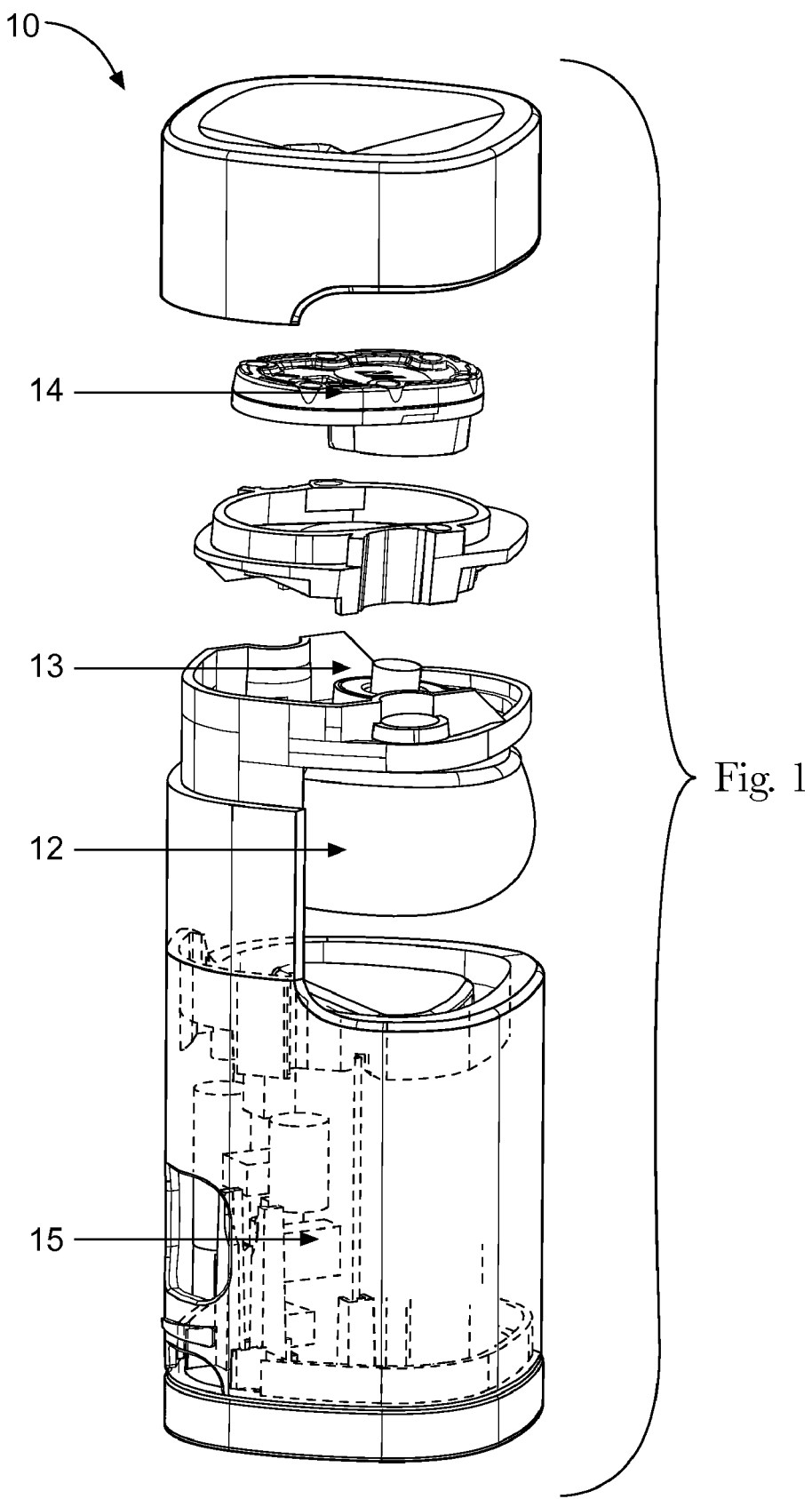
FIG. 1 is an exploded perspective view of one embodiment of a delivery system of the present invention.

Referring to FIG. 1 a non-limiting and exemplary delivery system 10 is shown. The delivery system 10 includes a liquid reservoir 12, which contains or may be provided with a liquid active material to be atomized. The reservoir 12 may be juxtaposed with and eccentrically or concentrically mounted below an electromechanical transducer 14 and droplet generation element.

A liquid supply component 13 may extend upwardly from within the reservoir 12 to the rear face of the droplet generation element or to a region in fluid communication with the droplet generation element. Upon activation of the electromechanical transducer 14, the liquid active material is generated through the droplet generation element, may be dispensed through an orifice, and into the atmosphere.

The reservoir 12 may comprise any liquid tight container suitable for holding an adequate quantity of the liquid active materials to be dispensed. The reservoir 12 may be pressurized or may be maintained at atmospheric pressure. Upon depletion of the reservoir 12, the reservoir 12 may be refillable with liquid active material provided from a bulk supply or the reservoir 12 may be replaced with a new reservoir 12 containing a quantity of liquid active material.

The liquid active material may be delivered to a droplet generation element by a liquid supply component 13 working by gravity feed, capillary action, pumping action, etc. If the droplet generation element is a perforate structure, the liquid supply component 13 may be disposed near the center of the droplet generation element so that the liquid supply component 13 may contact the perforations of the droplet generation element 8. However, the liquid supply component 13 need not contact the perforations and the perforations may be laterally displaced from the liquid supply component 13.

A continuous feed of the liquid active material from the reservoir 12 to the droplet generation element may be desired. The continuous feed may be accomplished by a using liquid supply component 13, which may comprise a feed tube that delivers liquid active material to the rear face of the droplet generation element or to a position juxtaposed with the rear face of the droplet generation element. The rear face of the droplet generation element is the face opposite from which the droplets may emerge. The liquid active materials may be delivered from the reservoir 12 to one face of the droplet generation element by a capillary feed. The capillary feed may be flexible and have a surface or assembly of surfaces over which liquid active material can pass from the reservoir 12 towards the droplet generation element. Exemplary capillary material forms include open cell foams, fibrous wicks, porous plastic wicks, and glass or polymeric capillary tubes.

Another approach to feed the liquid active material attempts includes the introduction of a space for containing the liquid, such that the apertured plate does not come into direct contact with the liquid conductor. In these developments liquid is transported from a reservoir 12 to the space via a fluidic channel which transports the liquid by way of capillary action in both vertical and/or lateral directions. The reservoir 12 can be present below the space, above the space, and/or laterally disposed from the space, as shown in WO 2007/062698 to Hess et al.; U.S. Pat. Nos. 6,196,219 and 6,405,934 both to Hess et al.; and U.S. Patent No. 2005/0230495 to Feriani et al.

For devices where the reservoir 12 is positioned such that at least a portion of the liquid contained within the reservoir 12 is above the space, the pressure on the liquid within the reservoir 12 from gravity can cause undesirable leakage out of the apertures of the apertured plate which is located in a lower position. Without the use of additional liquid flow control technologies, such as pressure control valves, the liquid leakage can make the device unacceptable in terms of performance and cleanliness. For devices, where the reservoir 12 is positioned below the space, the ability of the liquid conductor to draw the liquid from the reservoir 12 and provide it into the space is typically limited by the vertical distance which the liquid conductor can raise the specific type of liquid contained within the reservoir 12. As a result, reservoirs 12 which are typically shorter and wider are used to ensure that the liquid contained within the reservoir 12 is disposed a certain vertical distance from the perforated top plate.

The delivery system 10 may comprises a drive circuit 15. The drive circuit 15 may have an electromechanical transducer 14, which is an element capable of converting electrical energy to mechanical energy. One known example of an electromechanical transducer 14 comprises piezoelectric materials, which have the ability to change shape when subjected to an externally applied voltage. The voltage may cause the electromechanical transducer 14 to vibrate at certain frequencies. The electromechanical transducer 14 may be driven with an oscillating voltage or an AC at one of the resonant frequencies of the system or alternatively with a waveform that gives droplet on demand operation Forms of the electromechanical transducer 14 may include a plate, a rectangular cross-sectioned rod and a hollow tube with length greater than the separation between its inner and outer radii. In the case of the hollow tube, the electrodes are situated on the inner and outer walls and the device is poled radially. In the case of a rectangular cross-sectioned rod, the electrodes are situated on the two closest faces. This arrangement allows for the identification and operation at the system natural resonance frequencies, which is a more efficient mode than the typically used frequency sweeps. The benefit of this feature is that a given linear displacement of the electromechanical transducer 14 may be achieved by a smaller applied voltage. Another benefit is that the system can be operated with a less complex control strategy. Conveniently, the device may be run continuously at a frequency at which the displacements in the larger dimension of the electromechanical transducer 14 are in mechanical resonance. This may be at frequencies such that the resonance may be an acoustic mode or ultrasonic resonance mode of the device. Where the perforated structure induces only a perturbation to the electromechanical characteristics of the electromechanical transducer 14 (or in the complementary case where the electromechanical transducer 14 induces only perturbations to the mechanical characteristics of the perforated membrane) the device may be operated near one of the piezo resonance frequencies or one of the perforated structure resonance frequencies. The capability to be operated at the piezo resonance frequencies t allows the system to be driven and controlled by simpler and less expensive electronics.

The oscillating voltage may produce a vibration in the transducer 14. The vibration of the transducer 14 may, in turn, generate droplets of liquid active material through a droplet generation element, such as a perforate structure operatively associated with the electromechanical transducer 14. It is believed that a resultant pressure differential may be induced in the liquid directly behind a perforate structure. The resulting pressure differential may force the liquid through the perforations of a perforate structure to form droplets. The droplets of liquid active material may then be distributed to the atmosphere.

As noted above, the electromechanical transducer 14 may comprise a piezoelectric material, which vibrates at a frequency, such as a resonant frequency or harmonic thereof, under an externally applied voltage. The electromechanical transducer 14 may comprise various shapes and forms, such as a round disc having a hole concentrically or eccentrically therethrough. Electromechanical transducers 14 according to the present invention can be made of any material capable of converting electrical energy to mechanical energy. Examples of suitable electromechanical materials include, but are not limited to, piezoelectric materials, including ceramic materials such as available from Morgan Unilator of the UK (PC 5) or any other material having piezoelectric properties, which cause dimensional changes in the presence of an applied electric current. The dimensional change may be perpendicular to the direction of an applied electric field. The electromechanical transducer 14 element may expand and contract in a radial direction when an alternating electrical field is applied on poled electrodes.

A disc-shaped transducer 14 may have two opposed faces. A separate electrode may be disposed on each face and be radially poled. The electrodes may excite the length modes of the disc shaped transducer 14 or a mode of a perforate structure. The electrodes may be patterned so as to incorporate "drive" and "sense" electrodes, as is known in the art. The drive and sense electrodes are electrically insulated but mechanically coupled through the piezoelectric transducer 14. A drive voltage may be applied to the drive electrode. The resulting motion in the transducer 14 generates a voltage at the sense electrode. This voltage can then be monitored and used to control the drive voltage through a feedback circuit. The electrical response may be used to adjust the voltage to achieve specified resonances either by phase locking, amplitude maximizing or other known means. In order to maximize the electromechanical coupling to the desired mode it may be useful to shape the drive electrode appropriately.

The induced vibration may have an amplitude and phase induced in relation to characteristics of the drive signal. If desired, the drive voltage may sweep various frequencies, to provide a range of dispensing characteristics. Alternatively, the drive voltage may excite the transducer 14 at a single frequency. The single frequency may be coincident or near the transducer 14 natural frequency or a harmonic thereof. This arrangement may provide the benefit that less power is consumed than using a sweep of multiple frequencies over a spectrum.

The droplet generation element may be formed from a variety of materials including electro formed nickel, etched silicon, stainless steel or plastics. The droplet generation element may be relatively flexible or stiff. A flexible design is one where the amplitudes of the vibrational modes of the droplet generation element are large compared with those of the electromechanical transducer 14. The resulting motion may have a significant effect on the droplet generation process. A stiff design is one where the amplitudes of the vibrational modes of the perforate structure are generally equal to or smaller than those of the electromechanical transducer 14.

The droplet generation element may be operatively associated with the electromechanical transducer 14. "Operatively associated" means that the droplet generation element is responsive to the activation of the electromechanical transducer 14 such that the liquid active material passes through the droplet generation element for diffusion into the atmosphere. In one embodiment, the droplet generation element is operatively associated with the electromechanical transducer 14 by being joined or coupled to one face of the electromechanical transducer 14 by adhesive, solder, etc. The droplet generation element may also be de-coupled from the electromechanical transducer 14, yet still be operatively associated with the transducer 14.

A "decoupled piezoelectric actuator" as used herein means that the piezoelectric actuator is not directly connected to an emitting orifice or perforate plate from which a liquid is emitted into the atmosphere. Further, a decoupled piezoelectric actuator does not vibrate the emitting orifice such that the vibration causes emission of liquid droplets from a device. Rather, a decoupled piezoelectric actuator vibrates the liquid to be dispensed from a device and forces the liquid out through an adjacent emitting orifice or perforate plate. One decoupled piezoelectric actuator arrangement is described in WO 2007/062698.

The droplet size may be determined by varying the cross sectional area of the exit of the perforations. Round perforations may have a diameter of about 1 to about 100 microns. In one embodiment, the diameter of the perforations may be less than about 30 microns, less than about 15 microns, between about 2 to about 10 microns, about 4 to about 8 microns, or about 5 to about 7 microns.

The perforations may be tapered to have a reduction in cross-sectional area in the flow direction, as is known in the art. so that the cross sectional area of the perforations decreases from the rear face to the front face of the perforate structure. Such a tapered perforation may reduce the amplitude of vibration of the perforate structure which is necessary in order to produce droplets of a given size, due to the reduction of viscous drag upon the liquid as it passes through such perforations. Consequently, a relatively lower excitation of the electromechanical transducer 14 may be used, thereby providing improved efficiency in creating the droplets to be dispensed. In the case of a coupled electromechanical transducer 14 and perforate structure, the relatively lesser excitation energy may enable the use of a relatively thick and more robust perforate structure from which satisfactory droplet production can be achieved, allowing use with liquids of relatively high viscosity lesser mechanical stresses in the perforate structure. In the case of a decoupled electromechanical transducer 14 and perforate structure, reduction of viscous drag may also result in improved efficiency.

The droplet generation element may also or alternatively be a non-perforate structure. For example, the liquid active material may be fed onto a face of the droplet generation element that is opposite the rear face. Droplets may then be generated by vibration of the droplet generation element whether it is bending, expanding, or vibrating in a bilateral or unilateral mode.

The delivery system 10 may have a first, disposable part, comprising the liquid and its container or liquid reservoir 12. The second part, may be reusable, and may comprise the electromechanical transducer 14, the droplet generation element, associated drive electronics and a power supply. Alternatively, the system may be discarded upon depletion of the liquid, or solid as in the case of a wax, etc. to be dispensed.

Figure 2:
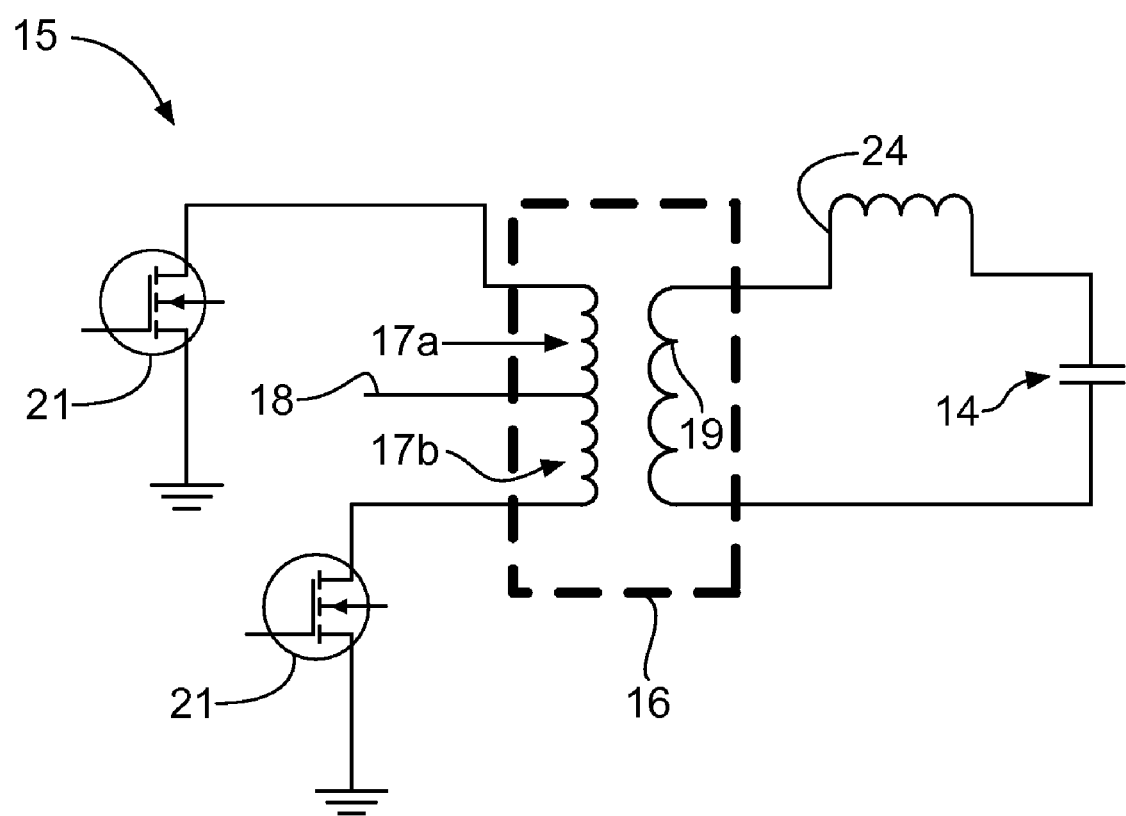
FIG. 2 is a circuit diagram of an exemplary power supply suitable for use with the present invention.

Referring to FIG. 2, the circuit 15 according to the present invention may comprise an input from a battery. The battery may provide a constant DC signal. The constant DC signal may be converted to a pulsating DC using a microprocessor. Two AA batteries battery and Sonix microprocessor, model no. SN8P2501B may be used.

Each of the pulsating DC signals from the microcontroller may be fed through an N Channel MOFSET transistor 21. The input signals may be fed into the gate of the transistor 21. The source of the transistor 21 is also connected to ground. Each drain from the transistors 21 may be fed to one side of the primary coil with the other side of the primary coil connected to a positive voltage supply. The input signals may be provided to the transformer 16 coils 180 degrees out of phase.

The primary windings 17a, 17b may conceptually be divided into two halves, a first half and a second half. The windings 17a of the first half may be wound clockwise, while the windings of the second half 17b, are counterclockwise, or vice versa. The first half and the second half of the primary windings 17a, 17b may be symmetrical, i.e. have an equal number of windings. This arrangement yields a symmetric sinusoidal output waveform. Alternatively, the first half and the second half of the primary windings 17a, 17b may have an unequal number of windings. This arrangement yields an asymmetric sinusoidal output waveform.

The first half and the second half of the primary windings 17a, 17b may have a common tap 18 to a positive power supply. This arrangement provides magnetic flux in two different directions in the core, one from each half of the windings. Superposition of the two signals 180 degrees out of phase results in more efficient operation, and hence a greater vibration amplitude of the piezoelectric transducer 14. The greater vibration amplitude results in a concomitant greater transfer of momentum from the piezoelectric actuator to the liquid active in a decoupled system, and/or to the droplet generation element in a coupled system.

The secondary windings 19 of the transformer 16 may be connected to the piezoelectric transducer 14 or other droplet generation element, as desired. An inductor 24 may be connected to the opposite side of the secondary coil, and wherein the inductor 24 and piezoelectric element 14 form the LC circuit.

The aforementioned inductor 24 may be tuned or selected to provide a desired frequency. The desired frequency may be coincident or near the resonant frequency of droplet generation element, or a harmonic thereof. The resonant frequency may be found using known methods, or as described herein below.

The circuit 15 may comprise an integrated electronic control circuit (not shown, but electrically upstream of the components in FIG. 2), a power supply that supplies power to the integrated electronic control circuit, a transformer 16 that receives power from the integrated electronic control circuit for powering a piezoelectric actuator. The piezoelectric actuator may be part of the integrated electronic control circuit. An integrated electronic control circuit is an electronic circuit that includes a microcontroller, a transformer 16, an inductor 24, and at least one passive component in electrical communication with the microcontroller. An integrated electronic control circuit includes a microcontroller that is capable of sending an electrical signal to a passive component and is also capable of receiving an electrical signal from a passive component. A passive component is an electrical building block that consumes energy but does not have an ASIC embedded therein.

The microcontroller may be programmed to provide the appropriate function for the desired drive circuit 15 or alternatively, the microcontroller may have a dedicated program embedded in ROM. The integrated electronic control circuit according to the present invention may power an actuating device. The microcontroller according to the present invention is configured to perform timing sequences to drive the piezoelectric element, drive signal, and perform the search algorithm to drive the piezoelectric element at its resonance frequency.

The present invention allows the capability of driving the piezoelectric element using a sinusoidal signal with the added flexibility of operation at high voltages. This arrangement provides an improvement over other power amplification circuits such, as an H-bridge or resonant bridge. As such, the present invention is able to drive the piezoelectric element using higher voltages which enable improved performance with respect to flow rate, plume height, and energy efficiency at equal or lower cost than other power amplification circuits.

For purposes of illustrating the present invention in detail, the present invention will be described in an air freshening system for generating liquid droplets of perfume materials. However, as stated above, those of ordinary skill in the art will understand that the present invention can be embodied in various actuating devices, and the invention is not limited to this specific execution. One of ordinary skill in the art will recognize that the benefits of the improved operation and reliability of the present invention can be applied to many actuating devices according to the present invention to power a piezoelectric actuator. More particularly, the actuating device according to the present invention may be powered at resonance.

Power Supply

The exemplary integrated electronic control circuit shown is driven by a power supply which may be an AC or DC power supply. Suitable power supplies include batteries and a standard wall outlet. The power supply may provide power to the microcontroller and a control power to at least one passive component. The drive power can optionally be provided first to an auxiliary power supply unit before being provided to the microcontroller.

Drive Circuit

The power supply may supply a drive power to the microcontroller which may include a drive signal generator. The microcontroller may have an internal drive frequency generator usable to generate a square wave drive signal with the frequency resolution required to drive the piezoelectric actuator. The drive signal generator may be programmed with software that will perform the function of frequency generation which uses the number of microcontroller clock cycles between output transitions to generate square waves that are required for driving the piezoelectric actuator. The resolution may be from about 16 MHz to about 1 KHz, depending on the timing of the clock.

The frequency of oscillation is a factor that affects power supplied to a piezoelectric actuator. The piezoelectric actuator may be operated at its resonant drive frequency. Suitable actuators may provide resonant drive frequencies in a range of about 40 KHz to about 220 KHz, alternatively about 80 KHz to about 100 KHz, alternatively about 80 KHz. When driven at the resonant frequency and a pre-determined voltage the power consumption of the piezoelectric actuator is usually at a maximum, compared to other frequencies at the same voltage.

To determine this resonant frequency, the final control power can be measured by turning off the control signal that drives the actuator for a predetermined number of cycles, such as 30 cycles, then turning the control signal back on and measuring the time to reach the target voltage in the capacitor. The frequency that takes the longest amount of time in a frequency sweep is the one that consumes the most power. The drive frequency generator may determine the frequency that consume the least piezoelectric actuator from the power supply to be the resonant frequency. The resonant frequency may be used for further operation to drive the piezoelectric actuator.

The device may have one or two calibration modes. When the device is switched on, the resonant frequency is unknown. Thus, before generating liquid droplets of perfume materials, all frequencies in the operating range may be tested as described above to find the desired operating frequency of the piezoelectric actuator. When operating, the resonant frequency may appear to shift, due to variation of circuit 15 parameters with temperature, etc. Therefore, each time the device generates liquid droplets, a single frequency point is measured. When all frequencies in the range have been measured, the operating frequency value is updated, and the process restarts.

Control Circuit

The power supply may provide control power of about 0.8 to about 15 volts DC, alternatively about 1.5 to about 3 volts DC, at an amperage of not to exceed about 800 mA, alternatively from about 200 to about 300 mA, feeding at least one passive component of the integrated electronic control circuit. In one embodiment, the passive component that receives control power from the battery may be an inductor 24. The passive component may have a relatively low quiescent power consumption power from the piezo crystal. The piezoelectric actuator current may be estimated by measuring the charge and discharge time of the capacitor as described below.

The microcontroller according to the present invention may contain all functional blocks desirable or required to implement not only the drive signal to drive the piezoelectric actuator, but also the control signal to generate sufficient voltage to power the piezoelectric actuator. A suitable microcontroller for the integrated electronic control circuit is, for example, a device known by the trade names of Atmel ATTINY13, ATTINY26L, Atmel Mega168, and Sonix SN8P2501B. The microcontroller may have fourteen pins with twelve IO pins.

Amplifier and Piezoelectric Actuator

The air freshening system may have a transformer 16 and a piezoelectric actuator. A transformer 16 may amplify the power supplied by the passive component. Upon receiving the drive signal from the microprocessor, the transformer 16 may send the final power signal to the piezo electric actuator.

In an air freshening system, the actuator may be a round piezoelectric crystal having a concentric, round orifice therethrough. The piezoelectric crystal may be mounted on a substrate having a perforate membrane from which liquid droplets of perfume materials are emitted or alternative it may be mounted on an opposite substrate from the substrate having the perforated membrane.

In such an embodiment, the transformer 16 may be configured as a dual input transformer 16 where in the inputs are wound in opposite directions with respect to current flow and the signals supplied to each input may be approximately or identically 180 degrees out of phase with respect to one another. This arrangement may generate a sinusoidal output sine wave at the actuator.

The output may be a single coil, where the winding ratio between the output and input provides a step up in voltage. The actuator forms part of the LC circuit. The drive signal generator may generate a drive signal which may be comprised of two signals 180 degrees out of phase at a desired frequency. Operating from about 3 to about 6 volts, such as about 3.5 volts, the microprocessor can generate a drive signal to the transformer 16 which amplifies the voltage to supply a final power to the actuator in the order of about 80 to about 170 volts peak-to-peak, alternatively about 90 to about 150 volts peak to peak. Power may be supplied to the actuator in the range of about 0.7 watts to about 1.7 watts Maintenance/Boost Modes In an air-freshener of this type, there may be a desire that the device sprays fluid in two different modes, in which case, the integrated electronic control circuit may include a maintenance switch and a boost switch. The maintenance switch may be connected to the microcontroller to control a timer provided by the microcontroller to set the interval at which the drive signal is provided to the power amplifier, in order to control the interval at which the droplet generator is automatically operated. The maintenance mode may be used wherein a preset quantity of fluid is emitted by the actuator over preset intervals.

The microcontroller may also provide a boost timer to generate the drive signal, on demand, as a pulse over a predetermined period longer than the pulse at which the piezoelectric actuator is automatically operated. The boost timer can be operated by a mono-stable boost switch connected to the microcontroller. The boost mode may be used when the user wishes to supplement the maintenance mode with an additional predetermined quantity of fluid emitted by the actuator.

Frequency Search Algorithm

Another embodiment of the present invention comprises an electronic drive system for a droplet spray generation device, wherein the droplet generator includes a perforate membrane actuated by a piezoelectric transducer 14; and wherein the electronic drive system comprises a programmable microcontroller, a power supply to power the device, a transformer 16 connected to receive electric power from the power supply via a capacitor and one or more components to generate one or more drive signals to drive the piezoelectric transducer 14; an electronic circuit designed to operate the power supply, in such a way as to control the charging of a capacitor to supply power to the transformer 16, which is connected to receive electric power from the capacitor and supply a drive signal to the piezoelectric transducer 14; wherein such electronic circuit may also be arranged to operate the transformer 16 and the drive signal at an operating frequency coincident or near its resonant frequency.

The resonant frequency may be determined by measuring timing changes to the voltage across the capacitor when the droplet spray generation device is actuated by a series of bursts at different frequencies, and by measuring the voltage drop across the capacitor at the end of the given time or by measuring the time taken to recharge the capacitor to the set value. The frequency at which the voltage drop, or the time to recharge the capacitor is the greatest, is determined as the resonance frequency.

The frequencies that the search algorithm checks are determined by using the frequency at which the microcontroller's crystal or resonator oscillates, known as main frequency. The main frequency is divided by an integer value (X). Using the following equation: Main Frequency/X=Drive Frequency, the microcontroller then varies X until the desired drive frequency is achieved. An example using a piezoelectric crystal having a 16 MHz main frequency is shown in Table I.

TABLE I

| Main Frequency | Denominator (X) | Drive Frequency |
|---|---|---|
| 16000000 | 230 | 69565.21739 |
| 16000000 | 229 | 69868.99563 |
| 16000000 | 228 | 70175.4386 |
| 16000000 | 227 | 70484.5815 |
| 16000000 | 226 | 70796.46018 |
| 16000000 | 225 | 71111.11111 |
| 16000000 | 224 | 71428.57143 |
| 16000000 | 223 | 71748.87892 |
| 16000000 | 222 | 72072.07207 |
| 16000000 | 221 | 72398.19005 |
| 16000000 | 220 | 72727.27273 |
| 16000000 | 219 | 73059.36073 |
| 16000000 | 218 | 73394.49541 |
| 16000000 | 217 | 73732.71889 |
| 16000000 | 216 | 74074.07407 |
| 16000000 | 215 | 74418.60465 |
| 16000000 | 214 | 74766.35514 |
| 16000000 | 213 | 75117.37089 |
| 16000000 | 212 | 75471.69811 |
| 16000000 | 211 | 75829.38389 |
| 16000000 | 210 | 76190.47619 |
| 16000000 | 209 | 76555.02392 |
| 16000000 | 208 | 76923.07692 |
| 16000000 | 207 | 77294.68599 |
| 16000000 | 206 | 77669.90291 |
| 16000000 | 205 | 78048.78049 |
| 16000000 | 204 | 78431.37255 |
| 16000000 | 203 | 78817.73399 |
| 16000000 | 202 | 79207.92079 |
| 16000000 | 201 | 79601.99005 |
| 16000000 | 200 | 80000 |
| 16000000 | 199 | 80402.01005 |

TABLE I-continued

| Main Frequency | Denominator (X) | Drive Frequency |
|---|---|---|
| 16000000 | 198 | 80808.08081 |
| 16000000 | 197 | 81218.27411 |
| 16000000 | 196 | 81632.65306 |
| 16000000 | 195 | 82051.28205 |
| 16000000 | 194 | 82474.2268 |
| 16000000 | 193 | 82901.5544 |
| 16000000 | 192 | 83333.33333 |
| 16000000 | 191 | 83769.63351 |
| 16000000 | 190 | 84210.52632 |
| 16000000 | 189 | 84656.08466 |
| 16000000 | 188 | 85106.38298 |
| 16000000 | 187 | 85561.49733 |
| 16000000 | 186 | 86021.50538 |
| 16000000 | 185 | 86486.48649 |
| 16000000 | 184 | 86956.52174 |
| 16000000 | 183 | 87431.69399 |
| 16000000 | 182 | 87912.08791 |
| 16000000 | 181 | 88397.79006 |
| 16000000 | 180 | 88888.88889 |
| 16000000 | 179 | 89385.47486 |
| 16000000 | 178 | 89887.64045 |
| 16000000 | 177 | 90395.48023 |
| 16000000 | 176 | 90909.09091 |
| 16000000 | 175 | 91428.57143 |
| 16000000 | 174 | 91954.02299 |
| 16000000 | 173 | 92485.54913 |
| 16000000 | 172 | 93023.25581 |
| 16000000 | 171 | 93567.25146 |
| 16000000 | 170 | 94117.64706 |
| 16000000 | 169 | 94674.55621 |
| 16000000 | 168 | 95238.09524 |
| 16000000 | 167 | 95808.38323 |
| 16000000 | 166 | 96385.54217 |
| 16000000 | 165 | 96969.69697 |
| 16000000 | 164 | 97560.97561 |
| 16000000 | 163 | 98159.5092 |
| 16000000 | 162 | 98765.4321 |
| 16000000 | 161 | 99378.88199 |
| 16000000 | 160 | 100000 |

A frequency search procedure may be used to determine the resonant frequency of the droplet spray generation device at which maximum power is consumed by estimating the power consumed at each test frequency by charging the power supply capacitor to a set voltage, switching the output on for a predetermined period of time, and then measuring the time taken for the capacitor to be recharged. The test frequency with the longest recharge time or at which more voltage is consumed is then set as the resonant frequency.

A second method to estimate the power consumed at each test frequency is to charge the power supply capacitor to a set voltage, switch the output to on for a set time, and then measure the capacitor voltage. The test frequency at which the lowest voltage value is measured is then determined as the resonant frequency.

Frequency Search Subroutine

The resonsant frequency may be in range of about 75 to about 90 KHz. When operated at its resonant frequency, the power consumption of the transducer 14 is at a maximum. This resonant frequency may be determined by measuring the time taken for the capacitor to recharge to the supply voltage and it may be measured as described below.

A high impedance voltage divider may be disposed across the capacitor and designed so that its output voltage is 2.5 volts when the capacitor is fully charged. The voltage divider output is connected to one input of a TL431A which serves as a comparator and a buffer. The output of the TL431A is connected to an IO pin of the microcontroller. Software running on the micro-controller is thus able to detect when the output of the voltage divider exceeds 2.5 volts and this indicates that the capacitor is fully charged.

In order to set the operating frequency, the microcontroller measures the time to recharge the capacitor for each of the test frequencies f of the voltage applied to the spray head executing the following routine:

At time t=0, microcontroller switches on the power supply unit (PSU) if external, or turns on power supply algorithm, if integrated.

Microcontroller keeps PSU ON for 1 millisecond, e.g. longer than required to charge the capacitor to ensure the capacitor fully recharged, if PSU is external or simply waits for the capacitor full feedback signal, if PSU is integrated.

Microcontroller switches off the PSU (V psu), time=0.9 millisecond

Microcontroller switches on the transformer 16 to drive the spray head to spray at the particular test frequency f for 1 millisecond, time=1.0 millisecond After the 1 millisecond spray, the microcontroller then switches on the PSU (internal or external) and measures the time it takes to charger the capacitor back to the target voltage.

The microcontroller then uses the external comparator, for example a TL431A to search for a suitable number, such as five to ten consecutive voltage divider readings greater than the threshold voltage, e.g. 2.5 volts. The microcontroller then stores the value of time to reach this point and the related test frequency f. The routine repeats this procedure for each of the test frequencies, until all the test frequencies have been tested. Once all the frequencies of f have been tested the microcontroller then sets the operating frequency to be the test frequency f corresponding to the longest capacitor recharge time.

During Operation Two Calibration Modes are Possible:

1. at start up, the resonant frequency is unknown, requiring all frequencies in the range to be tested as described above to find the desired operating frequency of the spray head. When all frequencies in the range have been tested, the operating frequency value is selected, and the system moves to continuous operation using the selected frequency as the resonance frequency.

2. at normal operation after start up, the resonant frequency may shift due to variation of circuit parameters. Therefore, to ensure that the device continues to work at its resonant frequency, four 1 millisecond pulses will be fired before each spray pulse. After the fourth 1 millisecond pulses, the frequencies tested are evaluated and the operating frequency value is updated, and the system will spray at the updated operating frequency. The process of four 1 millisecond pulses and one spray repeat until the system is turned off. The explanation of these four pulses is given bellow.

The four pulses may form two different algorithms. The first three pulses allow the device to adjust quickly to a new resonant frequency in the event the resonant frequency of the device change. The benefits of the fourth pulse is that it has the capability to adjusts to situations wherein the system get caught in a minima or low point in the impedance curve that may not necessarily be the lowest point on the impedance curve (lowest point on impedance curve=point of highest voltage at the piezoelectric head). The three pulses represent 1. (Resonant frequency−1 step) 2. (Resonant frequency) and 3. (Resonant frequency+1 step). A step represents the different exemplary frequencies listed in the above frequency table. The recharge times for each of the three pulses are compared to one another and the one with the longest time is the new resonant frequency. The spray pulse that follows the four pulses will be at the new resonance.

The fourth pulse may be a separate algorithm that checks each frequency in the frequency table. One benefit of this approach is that it is very thorough, and checks many possible frequencies but may be slow to adjust should the resonant frequency of the device change. This algorithm is illustrated below:

In both cases, (start up algorithm and ongoing algorithm) once all desired frequencies have been tested, the microcontroller sets the operating frequency to be the test frequency f corresponding to the longest capacitor recharge time. As mentioned above, the system has two calibration modes: when the system is switched on, the resonant frequency is unknown. So, before spraying a fluid, all frequencies in the range may be tested as described above to find the desired operating frequency, or frequency range, of the spray head.

In an alternative embodiment, a voltage-measuring solution is similar to the system described above, with the central timing loop replaced by a voltage measurement via the microcontroller's built-in analogue to digital converter. The algorithm searches for the lowest voltage, measured just after the 1 millisecond test spray pulse.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electronic driving circuit coupled to an air treatment device for emitting an air treatment into a space, said driving circuit comprising:

an actuating element and a power source, said actuating element comprising a piezoelectric element, wherein said piezoelectric element comprises a round piezoelectric disc having a round hole concentrically disposed therethrough, said piezoelectric element being juxtaposable with the air treatment material;

a step up transformer, said transformer having a dual input with clockwise and counter-clockwise windings and a common center tap in electrical communication with a power supply;

two input signals provided to the transformer 180 degrees out of phase with each other, and wherein said transformer provides an AC signal to said piezoelectric element; and an inductor connected to the transformer and disposed intermediate said transformer and said piezoelectric element;

wherein said inductor uses the AC signal generated by the transformer to drive the piezoelectric element with a substantially pure sinusoidal waveform, and wherein the inductor and the piezoelectric element comprises a LC circuit having a resonant frequency and being operable at a frequency generally equivalent said resonant frequency, thereby causing movement of said piezoelectric element relative to the air treatment material.

2. An electronic driving circuit according to claim 1, wherein said air treatment device is an air freshening system.

3. An electronic driving circuit according to claim 2 wherein said air freshening system comprises a liquid active material, said liquid active material is selected from the group consisting of perfumes, fragrances, insecticides, and mixtures thereof.

4. An electronic driving circuit according to claim 3 further comprising at least one passive component selected from the group consisting of a transistor, inductor, diode, capacitor, resistor, or combinations thereof.

5. An air treatment device for emitting an air treatment into a space, said device comprising:

an actuating element and a power source,
    said actuating element comprising a piezoelectric element having a concentrically disposed hole therethrough, said piezoelectric element each having a resonant frequency, said piezoelectric element being juxtaposable with a fluid air treatment material, whereby movement of said piezoelectric element relative to the material causes the material to be expelled from said device;
    said power source comprising a transformer having two input coils, a first input coil with clockwise windings and a second input coil with counter-clockwise-windings, said input coils being joined at a common tap electrically connected to a power supply, and an output, wherein said transformer provides a sinusoidal AC signal from said output to said piezoelectric element, said signal having a frequency generally equivalent to said resonant frequency of said piezoelectric element or said driver, thereby causing movement of said piezoelectric element relative to the material.

* * * * *